United States Patent
Frid

[19]

[11] Patent Number: 6,051,021
[45] Date of Patent: Apr. 18, 2000

[54] SELF-EXPANDING ENDOPROSTHESIS

[75] Inventor: Noureddine Frid, Beersel, Belgium

[73] Assignee: Medicorp, S.A., Cedex, France

[21] Appl. No.: 09/083,974

[22] Filed: May 26, 1998

[30] Foreign Application Priority Data

May 27, 1997 [BE] Belgium ............... 09700461
Sep. 2, 1997 [EP] European Pat. Off. ........... 97202698

[51] Int. Cl.$^7$ .............. A61F 2/06; A61F 2/04; A61M 29/00
[52] U.S. Cl. ............... 623/1; 623/12; 606/195; 606/198
[58] Field of Search .......... 623/1, 12; 606/195, 606/198

[56] References Cited

U.S. PATENT DOCUMENTS

| | | |
|---|---|---|
| 4,425,908 | 1/1984 | Simon . |
| 4,503,569 | 3/1985 | Dotter . |
| 4,512,338 | 4/1985 | Balko et al. . |
| 4,580,568 | 4/1986 | Gianturco . |
| 4,655,771 | 4/1987 | Wallsten . |
| 4,665,906 | 5/1987 | Jervis . |
| 4,681,110 | 7/1987 | Wiktor . |
| 4,743,251 | 5/1988 | Barra . |
| 4,795,458 | 1/1989 | Regan . |
| 4,954,126 | 9/1990 | Wallsten . |
| 5,037,427 | 8/1991 | Harada et al. . |
| 5,061,275 | 10/1991 | Wallsten ........................... 623/1 |
| 5,067,957 | 11/1991 | Jervis . |
| 5,190,546 | 3/1993 | Jervis . |
| 5,197,978 | 3/1993 | Hess . |
| 5,201,901 | 4/1993 | Harada et al. . |
| 5,226,913 | 7/1993 | Pinchuk . |
| 5,354,309 | 10/1994 | Schnepp-Pesch et al. . |
| 5,395,390 | 3/1995 | Simon . |
| 5,405,377 | 4/1995 | Cragg . |
| 5,534,007 | 7/1996 | St. Germain et al. ........... 606/108 |
| 5,540,712 | 7/1996 | Kleshinski . |
| 5,540,713 | 7/1996 | Schnepp-Pesch et al. . |
| 5,554,181 | 9/1996 | Das . |
| 5,562,725 | 10/1996 | Schmidt et al. . |
| 5,562,728 | 10/1996 | Lazarus et al. . |
| 5,575,818 | 11/1996 | Pinchuk .............................. 623/1 |
| 5,597,378 | 1/1997 | Jervis . |
| 5,624,508 | 4/1997 | Flomenblit et al. ............. 148/510 |
| 5,630,840 | 5/1997 | Mayer . |
| 5,674,277 | 10/1997 | Freitag . |
| 5,718,159 | 2/1998 | Thompson ........................... 87/33 |
| 5,741,333 | 4/1998 | Frid . |
| 5,758,562 | 6/1998 | Thompson ........................... 87/33 |
| 5,782,741 | 7/1998 | Bradshaw et al. .................. 600/3 |
| 5,840,387 | 11/1998 | Berlowitz-Tarrant et al. ...... 428/36.91 |
| 5,851,217 | 12/1998 | Wolff et al. ..................... 606/191 |
| 5,888,201 | 3/1999 | Stinson et al. ...................... 623/1 |

FOREIGN PATENT DOCUMENTS

| | | |
|---|---|---|
| 1205743 | 9/1970 | European Pat. Off. . |
| 0744164 | 5/1996 | European Pat. Off. . |
| WO 9219310 | 11/1992 | WIPO . |
| WO 9530385 | 11/1995 | WIPO . |
| WO 9531945 | 2/1996 | WIPO . |
| WO 9713475 | 4/1997 | WIPO . |

*Primary Examiner*—Michael J. Milano
*Assistant Examiner*—Hieu Phan
*Attorney, Agent, or Firm*—Roylance, Abrams, Berdo & Goodman, L.L.P.

[57] ABSTRACT

A luminal endoprosthesis comprising a framework made up of braided filaments. The framework is self-expanding, that is to say that after it has been radially compressed for positioning of the endoprosthesis, it automatically recovers its nominal diameter. The metal of the framework has undergone a thermal treatment bringing about a state transition, at a temperature close to that of the organism, and this confers upon it a suitable rigidity after it has been positioned in an anatomical conduit.

21 Claims, 3 Drawing Sheets

SELF-EXPANDING ENDOPROSTHESIS

FIELD OF THE INVENTION

The invention relates to radially expandable luminal endoprostheses and more particularly to vascular endoprostheses, and especially stents.

BACKGROUND OF THE INVENTION

Since the work done by C. DIDCOTT on the dilation and the support of anatomical conduits, the concept of dilatable endoprostheses has enjoyed great success.

One of the most remarkable breakthroughs in this field concerns in particular cardiovascular surgery, especially the reduction of aneurysms and the opening of stenoses.

A consequence of the general rate of success of these methods has been increasing demands on the part of practitioners, both as regards the quality of the products brought onto the market, and also their ease of use.

Crucial criteria in this regard include the high ratio between the diameter of the endoprosthesis in its contracted shape and its nominal diameter (unconstrained state), but also the flexibility of this endoprosthesis, which must be able, during insertion, to follow sinuous courses without thereby causing kinking.

Furthermore, when it is in place, such an endoprosthesis must demonstrate mechanical characteristics compatible with those of the vessels being treated, and it must be able to withstand the crush stresses generated by the ambient pressure and by the presence of adjacent organs.

Research initially focused in particular on blood vessels of small and medium calibre, but much remains to be done in the field of vessels of very small diameter and, by contrast, in anatomical conduits of large diameter.

Treating thoracic and abdominal aneurysms thus requires the use of endoprostheses of large diameter: of the order of 35 to 45 mm for thoracic aneurysms, and of the order of 22 to 33 mm for abdominal aneurysms.

None of the endoprostheses available on the market in this diameter range entirely satisfies the expectations of practitioners at the present time, essentially because they are unable to fulfil their role long-term, they are not easy to use, or else because the materials used are not suitable.

The endoprostheses used to repair the anatomical conduits comprise a rigid framework which is often provided with a coating. The endoprostheses consisting is solely of a framework bear the name "stent".

There are basically two types of frameworks (or stents) on the market, namely frameworks which are dilated by inflatable balloons, and self-expanding frameworks which comprise braided or unbraided structures.

Endoprostheses are known which are put in place and then dilated to their nominal diameter by introduction of an inflatable balloon.

Particular disadvantages of this technique are the interruption in the blood flow and the dimensions of the framework.

The balloon stents can only be used for treating lesions in arteries of small calibre (at most 12 mm). The reason for this is simple: for a stent with, for example, an initial diameter of 3 mm to be dilated up to a diameter of 8, 10 or even 12 mm, it is necessary to use a pressure of up to 5 to 10 atmospheres (as indicated in U.S. Pat. No. 4,950,227).

The balloon must therefore be extremely strong, which entails problems as regards diameter.

Furthermore, it is not possible to treat long lesions using this technique.

It should be noted that an intervention performed on an abdominal aneurysm can last for 6 to 8 hours when using a femoral or iliac surgical approach (compared to an average duration of 2 hours for treatment by a direct surgical route).

As regards the self-expanding stents, these do not require balloons: they are generally stretched out lengthwise and introduced, in a shape with a reduced diameter, into an applicator consisting of a tubular catheter equipped with a pusher. The whole assembly is introduced, particularly by the femoral or iliac route, as far as the deployment site, where the endoprosthesis is released.

Although they have some advantages, the known models of self-expanding stents also have a number of limitations, long regarded as insurmountable. Their diameter does not generally exceed 25 mm.

The braided stents with cobalt/nickel/chromium alloys (ELGILOY® or PHYNOX®), however, permit diameters varying from 2 mm to 45 mm or even 50 mm to be obtained.

Upon release, the endoprosthesis, initially subjected to elongation, with narrowing of its diameter, automatically recovers its nominal diameter.

The first braided endoprostheses of this type were made by C. DIDCOTT.

FR-1,602,513 discloses endoprostheses provided with a rigid framework which is formed by interweaving metal filaments into a braid. This document describes braids having an angle of intersection $\alpha$ of between 45 and 90° between the filaments of two different layers.

It goes without saying that, strictly from the mechanical point of view, a braid resists crushing less effectively, the more the braided filaments from which it is built deviate from a quasi-annular structure, namely a spiral of very small pitch, corresponding to an angle as close as possible to 90° relative to the axis of the braid angle (meaning that angle $\alpha$ between filaments should be as close as possible to 180° C. i.e. actually around 120° C.) (as described in FR-2,333,487). The smaller this angle, the less effectively the braid resists crushing.

Patent U.S. Pat. No. 5,061,275 describes an endoprosthesis with a braided framework in which the angle of intersection $\alpha$ is obtuse. In this case, the coefficient of elongation of the prosthesis is high, which entails problems when it is being put into place. (Coefficient of elongation is defined as the ratio of the axial extension of such a prosthesis in its stressed shape, hence with reduced diameter, and in its unstressed shape, at its nominal diameter).

Releasing this type of endoprosthesis therefore requires long practice, as pinpointing it is difficult (the endoprosthesis undergoes considerable shortening at the moment of its release). The endoprosthesis takes up a substantial length in the introducer, which creates friction and reduces manoeuvrability.

Research workers who have set themselves the task of solving the problems associated with the use of self-expanding prostheses with mechanical action have come up against questions relating to the angle, thickness and composition of the filaments, without managing to obtain a prosthesis bringing together all the quality criteria: it has not been possible to obtain a prosthesis combining a low angle of intersection and good resistance to crushing.

It will also be noted that for a same angle $\alpha \approx 85°$, a braid with 32 filaments presents a resistance to radial pressure which is 50%) higher than a braid with 24 filaments of identical diameter, a fact which shows that such a structure responds to relatively complex relationships.

EP-A-0 740 928 describes a braided endoprosthesis made of cobalt/nickel/chromium-based alloy, in which, in order to increase the resistance to radial compression, a doubled filament has been used, which poses a problem as regards the space taken up in the applicator.

The use of such filaments for making medical braids should in principle give good results. However, the limit of resistance to rupturing of the cold-hammered filament is situated at about 2000 N/mm$^2$ and, after thermal treatment, the filament reaches values of resistance to rupture of 2500 to 2700 N/mm$^2$, which makes the filament rigid and brittle; they prove relatively difficult to wind up and braid on account of their inherent elasticity. Frequent breaking of the filaments spoils in particular the spindles of the machines, which are subjected to accelerated deterioration.

In addition, when used long-term, especially for vascular conditions where the stresses on the metal are very high (e.g. abdominal aneurysms), it was found that the stents made from these filaments aged rapidly (effects of fatigue).

Fatigue tests have shown the same results after simulated longitudinal compression for an equivalent period of five months.

Other self-expanding endoprostheses described for instance in U.S. Pat. No. 5,354,309 and U.S. Pat. No. 5,540,713 are characterized by memory alloy part having a cylindrical jacket-shaped outer contour. For instance nickel/titanium alloys such as Nitinol® may be used.

Different shapes are known: truncated incised cylinders, helical structures, mesh structures, rolled-up metal sheets and the like.

When they reach the body temperature, they tend to adopt a radially expanded shape which a previous treatment has forced them to memorize. If they are not quickly brought up to the releasing site, they tend to pop up to their nominal diameter. It is therefore generally necessary to cool these endoprostheses and/or the applicator in which they are placed, as is also described in U.S. Pat. No. 5,037,427. In this document, the applicator of a memory-alloy stent is cooled throughout the placement phase by a ice-cooled physiologic saline. When the desired position is reached, the flow of cooling fluid is stopped and the stent, gradually warmed by the body heat, expands.

According to this method, it would be theoretically possible to remove the stent by cooling it again, so that it could be freely brought back to its reduced original diameter.

The truncated incised cylinders and the mesh structures generally lack flexibility, are rigid and kink excessively. There is thus a high risk that they damage the walls of the vessels. In addition, they take up considerable space in the introducer.

The helical structures (or coils) when triggered by the mere change of phase do not open the arteries sufficiently and are ineffective in the treatment of stenoses, since they do not cover the whole of the artery wall.

Furthermore, none of these endoprostheses types can be used in arteries of large calibre.

Moreover, it is necessary to anticipate the possibility that the stress force generated by the phase transition of the materials forming the framework is not sufficient to overcome the pressure due to the wall and the friction. In this case, there is a high risk of the endoprosthesis not being able to deploy.

The operator must anticipate the possibility of subsequent introduction of an inflatable balloon in order to bring the endoprosthesis to its nominal diameter. This technique of "forced" widening frequently leads, in the long term, to reactions by the organism (in particular tissue proliferation).

SUMMARY OF THE INVENTION

The object of the invention is to develop an endoprosthesis which exhibits high flexibility during its introduction, but which in situ exhibits good resistance, to crushing.

Another object of the invention is that the endoprosthesis exhibits good stability at the site of implantation.

Another object of the invention is to develop an endoprosthesis which covers a wide range of diameters and which can in particular be implanted in anatomical conduits of large diameter.

The subject of the invention is a luminal endoprosthesis comprising a multifilament braided framework made up of braided phase-transition metal filaments; said framework tends to spontaneously adopt, independent of its surrounding temperature, a given nominal diameter; the metal of the framework has undergone a suitable treatment conferring upon it, within a temperature range higher than ambient temperature and lower than the temperature of a warm-blooded organism, a structural state transition bringing it from a given rigidity to a greater rigidity.

The braid is made up of braided filaments which intersect at an angle $\alpha$ when the framework is at its nominal diameter. This angle can vary along the length of the braid. These filaments preferably form an angle $\alpha$ of between 30 and 95°, and advantageously between 50 and 90° along at least a section of the framework.

The metal is preferably superelastic, a property allowing it to deform reversibly by several percent. The filaments forming the braid are advantageously made of biocompatible metal, and are chosen from the nickel/titanium alloys and the nickel/titanium/cobalt alloys. The alloy preferably comprises between 52 and 56% by weight of nickel.

The invention also relates to a method for manufacturing an endoprosthesis as described hereinabove, comprising the following operations:

producing filaments made of an elastic metal on which it is possible to confer a reversible transition of atomic structure, causing it to change from a given rigidity to a greater rigidity, braiding these filaments around a mandrel in such a way as to obtain a braid of a given nominal diameter, subjecting sections of this braid, at their nominal diameter, to a thermal treatment establishing a phase transition at a temperature equal to or lower than the temperature of a warm-blooded organism, placing an optional coating on the said framework, cutting the sections of braid into segments of suitable length.

The braiding is advantageously effected using cold-hammered nickel/titanium filaments straight from the die, and the thermal treatment comprises at least one heating phase in a zone between 450 and 600°, advantageously at 500° C., for 10 minutes, and air cooling.

The braiding is advantageously carried out so that the filaments form between each other, at least along a section of the braid, a value of angle $\alpha$ between 30 and 95°.

Various advantages of the invention are that the endoprosthesis permits a greatly reduced coefficient of elongation, is very flexible in its contracted shape, is not prone to kinking and fully resists crushing after it has been put into place.

Another advantage is that below its transition temperature, the endoprosthesis is very easy to manipulate, so that it can readily be set to the right (nominal) dimension, brought to its reduced diameter and introduced into an applicator without fear of damage.

BRIEF DESCRIPTION OF THE DRAWINGS

Other features and advantages of the invention will be evident from the description of particular embodiments, with reference being made to the attached figures, of which.

DESCRIPTION OF THE EMBODIMENTS

Figure 1:
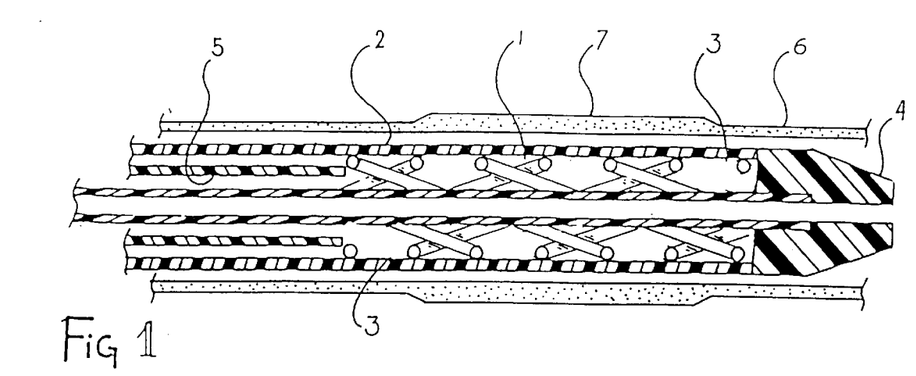
FIGS. 1 and 2 are diagrammatic representations of two stages in positioning an endoprosthesis according to the invention in an anatomical conduit.

FIG. 1 shows the general appearance of a device used for positioning an endoprosthesis according to the invention. For the sake of clarity of the drawings, only the framework 1 of the endoprosthesis is represented here. Of course, what appears here as a simple stent may include an external and/or internal coating.

The framework 1 is made up of a braid of interlaced metal filaments.

The particular feature of the endoprosthesis according to the invention lies in the design of its framework, which involves the effects of a braided, naturally elastic structure, and the particular physical properties of the filaments from which it is made, combined with a phase transition effect.

The filaments forming the braided framework are made from a specific alloy (in this case a Ni/Ti alloy) which, by virtue of a suitable treatment which is described hereinafter, undergoes, at a predetermined temperature, close to that of a warm-blooded organism, a reversible transition of its crystal structure, entailing a radical change in its mechanical characteristics.

The metal of the framework 1 in its initial state (that is to say, below its phase transition temperature) appears perfectly ductile.

Under these conditions, the operator can very easily manipulate the endoprosthesis without fear of damaging it, breaking up the structure or disrupting the arrangement of the filaments. He can in particular set the endoprosthesis to the appropriate dimension by cutting it and compressing it radially (the effect of which is to bring the filaments up close to one another, their angle of intersection tending at this moment towards a negligible value close to zero).

With the endoprosthesis in this state, the operator can easily pass it onto the hollow rod 3 of an applicator, between a non-traumatising tip 4 and a pusher 5, and slide onto it an outer sheath 2 which holds the endoprosthesis in place by subjecting it to a radial stress, at this stage virtually negligible. FIG. 1 shows the distal end of the applicator after the latter has been introduced percutaneously into an anatomical conduit 6, in such a way as to bring the endoprosthesis to the site to be treated 7.

At the instant when the operator releases the endoprosthesis by sliding the sheath 2 backwards, the radial stress ceases to apply, and, by virtue of the inherent elasticity of the braided structure, the framework 1 dilates to its nominal diameter, which corresponds substantially to that of the anatomical conduit 6.

Furthermore, the crystal structure transition mentioned above occurs when the temperature of the framework 1 reaches that of the organism.

This change exerts its effects at the moment when the framework 1 deploys, this corresponding to an increase in the value of the angle of intersection between the filaments.

The filaments thus participate in two ways in the opening out of the braided structure: there is an important synergistic effect between the deployment of the braided structure of the framework and the rigidification of the filaments due to their state transition.

The endoprosthesis which, until the moment of release, exhibited very great flexibility, perfectly adapted for its insertion into the sinuosities of anatomical conduits, is thus rigidified and, quasi-instantaneously, perfectly capable not only of exerting an adequate pressure on the inner wall of the anatomical conduit 6, but also of withstanding the external stresses which this anatomical conduit 6 will necessarily suffer.

The two combined effects (mechanical expansion coupled with thermal rigidification) reinforce each other and permit a complete expansion of the endoprosthesis without trauma, a fact which in the long term is beneficial to the patient.

For equivalent performances, the number of the filaments forming the framework 1 of the endoprosthesis can be reduced, or, optionally, it is possible to use filaments of smaller diameter than in the braided endoprostheses according to the prior art, which fact leads to a substantial reduction in the diameter of the stent in the compressed state, and thus of the applicator, and increases the flexibility.

This design also brings with it other appreciable advantages, particularly for the positioning in the anatomical conduits of large diameter.

If it is desired to treat lesions which are highly atheromatous, then, with endoprostheses using conventional self-expanding frameworks, this is only possible at the expense of a technology which can he described as onerous: these frameworks then have to be provided with strengthening elements which take up a large amount of space (relatively thick metal, large number of filaments and/or filaments of large diameter). Even in their radially contracted shape, such endoprostheses present a high diameter and length.

Using the endoprosthesis according to the invention, not only is the framework made light (hence a reduction of the diameter in the applicator), but in addition the risk of radial non-deployment of the endoprosthesis is considerably reduced.

Figure 2:
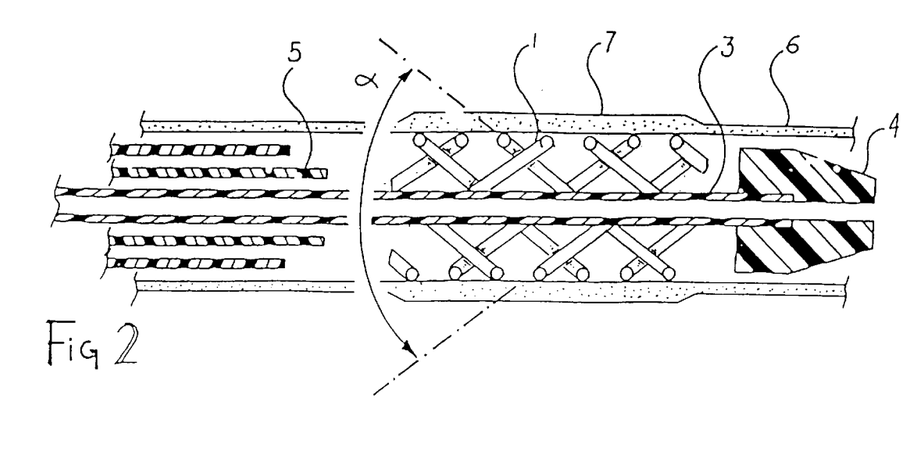

FIG. 2 shows the final angle $\alpha$ formed between the braided filaments when the framework is deployed radially.

The endoprosthesis in practice affords excellent results, independently of the value of the chosen angle. Trials have demonstrated excellent adaptation of the endoprostheses according to the invention, especially for values of $\alpha$ of between 30 and 95°, and, optimally, in a range of 50 to 90°. In this range of angles, the difference in length between the compressed endoprosthesis (see FIG. 1) and the released endoprosthesis (see FIG. 2) is proportionally small.

It will be noted that the diameter of the endoprosthesis (represented here as quasi-cylindrical) can vary along its length, and that as a consequence the angle $\alpha$ can also vary depending on the particular section of the endoprosthesis.

Figure 3:
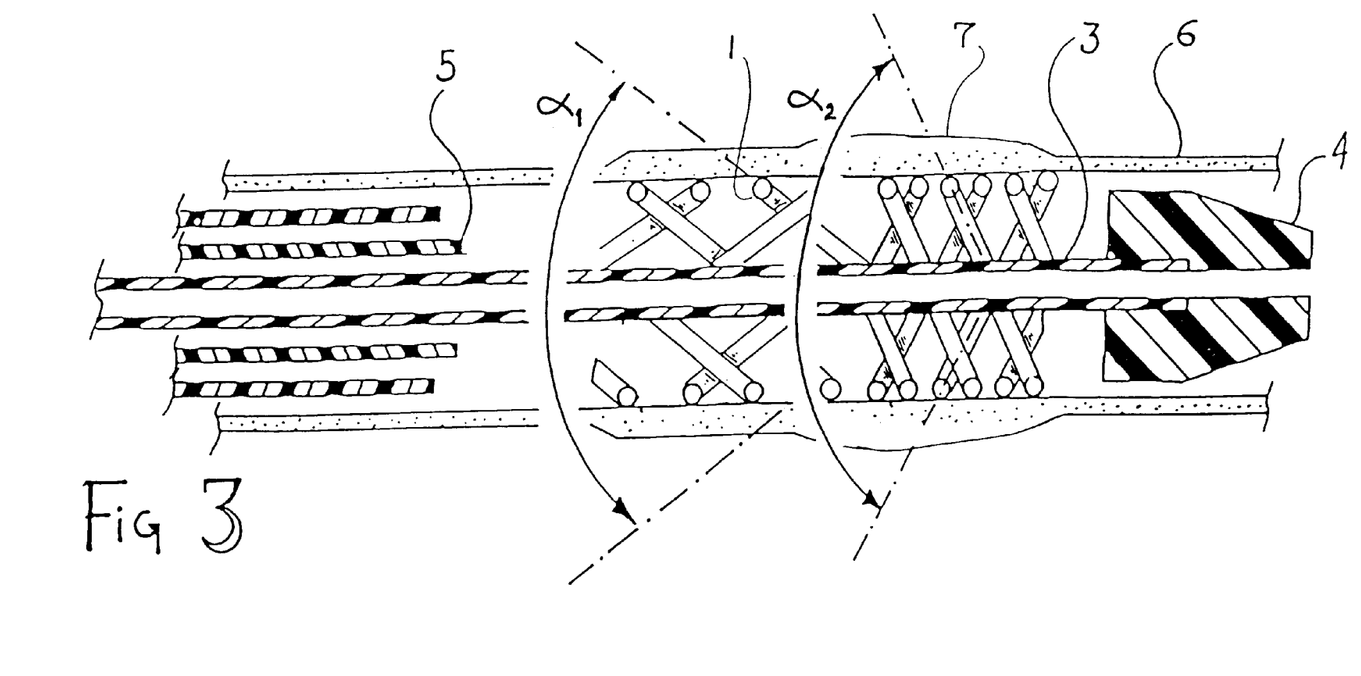
FIG. 3 is a diagrammatic representation of another embodiment wherein angle $\alpha$ varies along the length of the endoprosthesis.

FIG. 3 displays an endoprosthesis according to the invention, wherein the pitch varies along the length, causing $\alpha$ to adopt different values, in the present case $\alpha 1$ and $\alpha 2$.

A low value of $\alpha$ makes it possible to reduce in particular the phenomena of friction at the moment of release and to better adapt the endoprosthesis to the biomechanical characteristics of the anatomical conduits.

As was indicated hereinabove, the friction phenomena, which are characteristic of the endoprostheses having a high coefficient of elongation, did in fact limit up to now the treatment possibilities to lesions of small axial extension.

In addition, the positioning operations are made easier because of the enhanced flexibility, precision of positioning and reliability of the release manoeuvre.

Even in the case of a small angle of intersection $\alpha$ between the filaments, the clinical trials reveal what is at first sight a paradoxical effect: the endoprosthesis does not tend to migrate along the axis of the conduit, as the practitioner might expect it to do.

The manufacture of the framework of the endoprosthesis according to the invention involves a limited number of operations, which has favourable repercussions on the production costs.

Even after thermal treatment determining the temperature at which the state transition should take place, the present shape memory filament remains flexible and does not exhibit the rigidity of a traditionally conditioned shape-memory filament: it attains a resistance to rupture of barely 1500 $N/mm^2$.

The manufacture of the framework of an endoprosthesis according to the invention generally comprises the following operations:

producing filaments made of cold-hammered nickel/titanium alloy, braiding these metal filaments around a mandrel before annealing at the die outlet, cutting the braid into sections, subjecting sections of braid, at their nominal diameter, to a thermal treatment establishing a phase transition of the metal at a temperature equal to or lower than the temperature of the organism.

The origin of the shape memory is the existence of a reversible crystal change which takes place during cycles of heating/cooling of the specimen. In the case of metals, the high-temperature phase called austenite Is characterized by a unit cell of high symmetry (it occupies a greater volume without mass transfer). The low-temperature phase, called martensite, has a cell of lesser symmetry and occupies a minimum volume.

This phase may appear in several variants.

In order to obtain the change-over from one to the other of these two states in a perfectly reproducible manner, it is necessary to force the martensite in a single of several equivalent variants, in such a way as to obtain the appropriate rigidity of the metal contributing to the physical structure of the braid forming the framework.

The composition of the alloy (in which the nickel is present in a proportion varying between 52 and 56% by weight) plays an important role in determining the optimum parameters.

It has been found that a tiny variation in the composition is sufficient to shift by several degrees the temperature of the treatment necessary to obtain a given martensitic transformation. For example, a variation of 0.1% by weight of nickel entails a variation of 15° C. in the temperature of the thermal treatment. It is therefore expedient to look after the composition as well as the treatments when aiming to obtain a very precise martensitic transformation temperature and stable effects.

The braided structure is prepared by fixing it on a metal bar with a diameter in relation to the nominal diameter of the endoprosthesis, or by introducing It inside a hollow mould. The whole undergoes a thermal treatment at between 400 and 600° C. for an appropriate length of time (generally of the order of 10 minutes), which operation is followed by air cooling. The martensitic transformation temperature is then situated between 30 and 40° C. By way of example, for an alloy with 55.7% nickel, cold-hammered to 40%, a treatment time of 10 minutes at 500° C. is applied, and the maximum stiffening is obtained around 37° C.

As a function of the diameter of the filaments used, the thermal treatment can, if appropriate, be repeated in order to eliminate the residual austenite.

By way of comparison, the thermal treatment of ELGILOY® alloys used for classical braided stents must be carried out under vacuum at 550° C. and lasts ±4 hours.

As stated above, the present stent is also able to withstand very high radial solicitations.

Table 1 hereinbelow permits comparison of the resistance to radial pressure of various endoprosthesis frameworks.

The best known and easiest method is carried out with the aid of an INSTRON® extensometer apparatus.

The specimens are brought to a temperature of 37° C., either using a thermostatic bath or air. A very fine filament, of approximately 0.10 mm in diameter, is wound round each framework. One end of this filament is fixed to the base of the apparatus and the other is fixed to the upper part of the apparatus which is removable.

This upper part consists of a probe which simultaneously measures the force exerted on the specimens and the corresponding displacements.

The resulting value is determined (in Newton) using a computer program.

TABLE I

|  | Stents according to the invention (37° C.) | | Cobalt alloy stents | | |
| --- | --- | --- | --- | --- | --- |
| Value of angle α/2 | 32.5° | 35° | 45° | 55° | 53° |
| Length | 80 mm | 80 mm | 80 mm | 80 mm | 80 mm |
| Initial diameter (mm) | 8.1 | 30.1 | 8.15 | 8.2 | 30.5 |
| Radial Force N | Diameter under stress (mm) | | | | |
| 0 | 8.1 | 30.1 | 8.15 | 8.2 | 30.5 |
| 0,20 | 8.1 | 30.1 | 7.5 | 7.98 | 30.5 |
| 0,40 | 8.1 | 30.1 | 7.2 | 7.91 | 30.2 |
| 0,60 | 8.1 | 30.1 | 8.95 | 7.3 | 29.8 |
| 0,80 | 8.1 | 30.1 | 6.3 | 6.98 | 26.1 |
| 1,00 | 8 | 29.9 | 5.5 | 6.2 | 23.54 |
| 1,20 | 7.99 | 29.6 | 4.2 | 5.7 | 20.05 |
| 1,40 | 7.98 | 29.3 | 3.1 | 4.9 | 19.4 |
| 1,60 | 7.97 | 29.1 | 2.5 | 3.9 | 16.36 |
| 1,80 | 7.96 | 28.9 | 2.1 | 3.2 | 12.6 |

The table clearly shows that the stents according to the invention stay close to their nominal diameters under radial constraint sufficient to cause stents according to the state of the art, almost to collapse.

It will be noted that the nickel/titanium filaments used are covered, following the present thermal treatment, with a layer of titanium oxide which ensures the passivation of the metal (by way of comparison, the metal surfaces of cobalt alloy structures must be passivated by subsequent treatment with nitric or phosphoric acid).

The ends of conventional alloy frameworks are sharp and aggressive because of the rigidity of the filaments. Cases of perforation of arteries or of the sheath of the applicator are not uncommon.

By contrast, the endoprostheses provided with a framework according to the invention are non-traumatizing and simple to trim, which makes it easy to adjust their length from one case to another, if necessary at the actual site of an intervention, starting from segments of standardized length, which facilitates the packaging of the framework elements and of the endoprostheses themselves.

Figure 4:
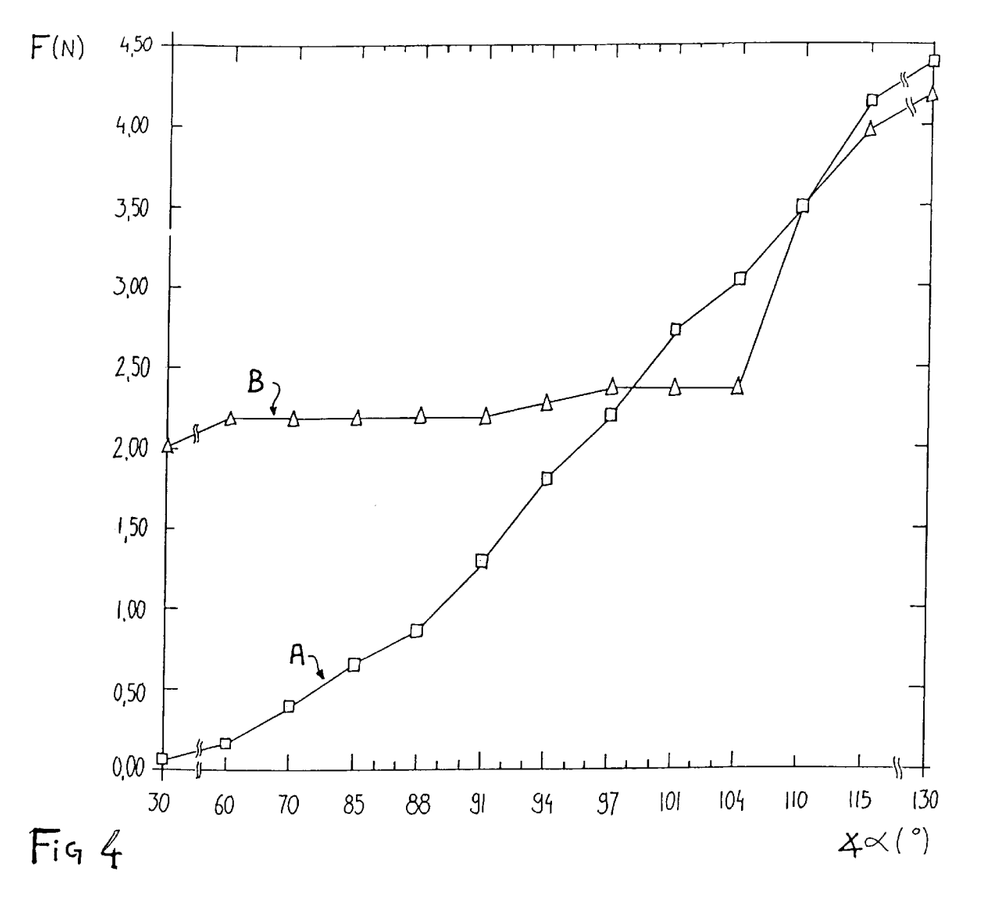
FIG. 4 is a graph showing the relationship between $\alpha$ (angle of intersection between two filaments of a stent) and the radial force (corresponding to the resistance of the stent to radial pressure thereof), established for a braided stent according to the state of the art and for a stent according to the invention.

The graph of FIG. 4 displays two curves obtained by measuring in an extensometer the values (expressed in Newton) of the radial force F (resistance to radial pressure) of stents braided at different pitches ($30°<\alpha<130°$) respectively from classical cobalt alloy wire (curve A) and from nitinol wire (curve B) as in the present invention other parameters remaining constant (i.e. stent diameter=8 mm, wire diameter=0,17 mm, number of wires=24).

As becomes directly apparent from the graph, curve A shows off a virtually linear relationship between angle $\alpha$ and the radial force F.

As discussed above, the higher the value of $\alpha$, the higher the coefficient of elongation of the stent.

As a consequence, the practitioner has to make a compromise when he opts for a given value of $\alpha$.

Curve B, on the contrary, exhibits a virtually constant value of F between 60° and 90° (flat segment of the curve), significantly above the corresponding values on curve A, then a slightly increasing value between 90° and 104°.

Above 105°, the mechanical effect of the geometry of the braided structure becomes predominant with respect to the thermal effect.

The practitioner thus has at his disposal a stent that simultaneously exhibits a high resistance to radial pressure and a low length decrease when released in place.

Moreover, clinical studies on the present stent brought out a particularly advantageous property thereof: its hysteresis cycle is astonishingly similar to the one of the vessels, allowing it to comply with the variations of diameter of the vessels according to the heart pulsations, accompanying them in their contraction-dilation cycle.

The present stent thus mimics an active component of the circulatory system. As a consequence, the possibilities of rejections and other side-effects are lowered.

Another proved advantage is that the stent remains even over long terms close to its nominal diameter while classical braided stents are known to have a tendency to distend the walls of the vessels, causing as a counter-reaction a stretch of the adjacent sections of the arteries.

I claim:

1. A luminal endoprosthesis, adapted for introduction into an anatomical conduit of an organism, comprising:
   a self-expandable braided framework of filaments, radially expandable to a nominal diameter, said filaments including a temperature transitionable material;
   said temperature transitionable material of said framework being adapted to experience a phase transition in which a rigidity of said transitionable material changes from a first rigidity to a second rigidity, greater than said first rigidity, at a temperature equal to or lower than a temperature of said organism; and
   said framework being compressible to a reduced diameter for introduction into said anatomical conduit of said organism, and upon release of compression, said framework being adapted to spontaneously adopt said nominal diameter independent of a temperature surrounding said framework and said phase transition.

2. An endoprosthesis according to claim 1, wherein at its nominal diameter, the braided filaments form between each other, along at least a section of the braid, an angle $\alpha$ between 30° and 95°.

3. An endoprosthesis according to claim 2, wherein the angle $\alpha$ is between 50 and 90°.

4. An endoprosthesis according to claim 2, wherein the angle $\alpha$ varies along the length of the braid.

5. An endoprosthesis according to claim 1, wherein the metal of the filaments is superelastic.

6. An endoprosthesis according to claim 5, wherein the metal of the filaments is chosen from the group consisting in the nickel/titanium alloys and the nickel/titanium/cobalt alloys.

7. An endoprosthesis according to claim 6, wherein the alloy comprises between 52 and 56% by weight of nickel.

8. Method for manufacturing an endoprosthesis according to claim 1, comprising the following operations:
   producing filaments made of an elastic metal on which it is possible to confer a transition of atomic structure, causing it to change from a given rigidity to a greater rigidity,
   braiding these filaments around a mandrel in such a way as to obtain a braid, of a given nominal diameter,
   subjecting sections of this braid, at their nominal diameter, to a thermal treatment establishing a phase transition at a temperature equal to or lower than the temperature of a warm-blooded organism,
   placing an optional coating on the said framework,
   cutting the sections of braid into segments of suitable length.

9. Method according to claim 8, wherein
   the braiding is effected using cold-hammered nickel/titanium filaments from the die, and in that
   the thermal treatment comprises at least one heating operation in a zone between 400° and 600° C., and air cooling.

10. Method according to claim 9, wherein the thermal treatment is carried out at 500° C. for 10 minutes.

11. Method according to claim 8, wherein the braiding is carried so that the filaments form between each other at least along a section of the braid, an angle $\alpha$ of between 30° and 95°.

12. An endoprosthesis as claimed in claim 1, wherein said nominal diameter of said framework varies along a length of said framework.

13. An endoprosthesis as claimed in claim 1, wherein said temperature at which said temperature transitionable material of said framework experiences said phase transition is 37° C.

14. A method of placing a self-expanding endoprosthesis in an anatomical conduit of an organism, said endoprosthesis being radially expandable to a nominal diameter and including a temperature transitionable material, said method comprising the steps of:
   placing said endoprosthesis in an environment having a temperature at or below a transition temperature at which said endoprosthesis experiences a phase transition in which a rigidity of said transitionable material changes from a first rigidity to a second rigidity, greater than said first rigidity, said transition temperature being a temperature equal to or lower than a temperature of said organism;
   compressing said endoprosthesis to reduce a diameter of said endoprosthesis from said nominal diameter to a reduced diameter for introduction into said anatomical conduit of said organism;

introducing said compressed endoprosthesis into said anatomical conduit; and releasing compression from said endoprosthesis to enable said endoprosthesis to spontaneously adopt said nominal diameter independent of a temperature surrounding said endoprosthesis and said phase transition.

15. A method as claimed in claim 14, further comprising the step of:

exposing said endoprosthesis to said temperature of said organism to enable said endoprosthesis to experience said phase transition in which said rigidity of said transitionable material changes to said second rigidity.

16. A method as claimed in claim 14, wherein said endoprosthesis includes a braided framework of filaments.

17. A method as claimed in claim 14, wherein said transition temperature is 37° C.

18. A luminal endoprosthesis, adapted for introduction into an anatomical conduit of an organism, comprising:

a self-expandable framework, radially expandable to a nominal diameter and including a temperature transitionable material;

said temperature transitionable material of said framework being adapted to experience a phase transition in which a rigidity of said transitionable material changes from a first rigidity to a second rigidity, greater than said first rigidity, at a transition temperature within a predefined temperature range; and said framework being compressible to a reduced diameter for introduction into said anatomical conduit of said organism, and upon release of compression, said framework being adapted to spontaneously adopt said nominal diameter independent of a temperature surrounding said framework and said phase transition.

19. A luminal endoprosthesis as claimed in claim 18, wherein said framework includes a braided framework of filaments.

20. A luminal endoprosthesis as claimed in claim 18, wherein said predefined temperature range is between 30° C. and 40° C.

21. A luminal endoprosthesis as claimed in claim 18, wherein said transition temperature is 37° C.

* * * * *

UNITED STATES PATENT AND TRADEMARK OFFICE
CERTIFICATE OF CORRECTION

PATENT NO. : 6,051,021
DATED : April 18, 2000
INVENTOR(S) : Noureddine Frid

It is certified that error appears in the above-identified patent and that said Letters Patent is hereby corrected as shown below:

On the Title Page

Please change Assignee's name to read:

MEDICORP R&D Benelux S.A.

Please change Assignee's residence to read:

Mons, Belgium

Signed and Sealed this

Twenty-second Day of May, 2001

*Attest:*

NICHOLAS P. GODICI

*Attesting Officer*     *Acting Director of the United States Patent and Trademark Office*